United States Patent [19]

Nycz et al.

[11] Patent Number: 5,314,801
[45] Date of Patent: May 24, 1994

[54] **PROBES TO *MYCOBACTERIUM AVIUM, MYCOBACTERIUM INTRACELLULARE,* AND *MYCOBACTERIUM PARATUBERCULOSIS***

[75] Inventors: Colleen M. Nycz, Raleigh; James L. Schram, Knightdale; Daryl D. Shank, Durham; Glenn P. Vonk, Fuquay-Varina, all of N.C.

[73] Assignee: Becton, Dickinson and Company, Franklin Lakes, N.J.

[21] Appl. No.: 973,342

[22] Filed: Nov. 6, 1992

[51] Int. Cl.⁵ .............. C12Q 1/68; C12P 19/34; C07H 21/00
[52] U.S. Cl. .............. 435/6; 435/91.2; 536/24.32; 536/24.33; 935/78
[58] Field of Search .............. 435/6, 91, 91.2; 536/23.7, 24.32, 24.33; 935/77, 78

[56] References Cited

PUBLICATIONS

Walker et al. Proc. Natl Acad. Sci USA (1992) 89:392–396.
Vary et al. J. Clin. Microbiol (1990) 28:933–937.
Conville, Dragh Microbiol Infect. (1989) 12:217–219.
Rogall et al. Int. J. Syst Bacteriol (1990) 40:322–330.
Ellis et al. Nucl Acids Res 1986 14:2345–2364.
J. W. U. Fries, et al. "Genus-and Species-Specific DNA Probes to Identify Mycobacteria Using the Polymerase Chain Reaction" Molecular and Cellular Probes 4,87–105 (1990).

*Primary Examiner*—Margaret Parr
*Assistant Examiner*—Carla Myers
*Attorney, Agent, or Firm*—Donna R. Fugit

[57] ABSTRACT

The invention provides methods and nucleic acid probes for deleting, amplifying, and isolating sequences of *Mycobacterium avium, Mycobacterium intracellulare,* and *Mycobacterium paratuberculosis.*

24 Claims, No Drawings

PROBES TO MYCOBACTERIUM AVIUM, MYCOBACTERIUM INTRACELLULARE, AND MYCOBACTERIUM PARATUBERCULOSIS

FIELD OF THE INVENTION

The invention is in the field of molecular biology. In particular, the invention relates to diagnostics involving nucleic acid probes. More particularly, the invention relates to nucleic acid probes for detecting, amplifying, and isolating Mycobacterium avium, Mycobacterium intracellulare, and Mycobacterium paratuberculosis.

BACKGROUND OF THE INVENTION

Health care providers are encountering a significant increase in cases of mycobacterial infections. Many of these new cases are related to the AIDS epidemic. Physicians rely on clinical microbiologists to assist them in diagnosing mycobacterial infection. The diagnosis of such infections is, however, largely dependent on acid fast staining and cultivation of the organism, followed by biochemical assays. These are time consuming processes. Hence, there is a continuing need for new, and particularly rapid, methods of diagnosing mycobacterial infections.

SUMMARY OF THE INVENTION

The present invention provides nucleic acid probes and methods that are definitive, rapid, and cost effective for detecting, amplifying, and isolating Mycobacterium avium, Mycobacterium intracellulare, and Mycobacterium paratuberculosis. The invention also provides methods for isolating sequences of M. avium, M. intracellulare, and M. paratuberculosis. In addition, probes of the invention are useful for amplification of sequences to which they hybridize.

Probes of the invention can also be used to construct amino acid sequences for which they encode and antibodies raised to recognize the sequence.

Probes of the invention consist essentially of the nucleic acid sequences in Seguence ID No: 1-15. The probes can locate either M. avium, M. intracellulare or M. paratuberculosis or any combination thereof. Since the probes of the invention are unique, there is no cross hybridization to nucleic acid from other microorganisms.

The probe sequences described in the invention are derived from plasmid pMav29 originally identified by Fries et al., Molec. Cell Probes 4:87 (1990). Plasmid pMav29 had cross-reactivity to M. intracellulare and M. avium, but also strong cross-reactivity to M. bovis and lesser cross reactivity to M. tuberculosis. The probes described in this invention offer substantial improvement over that described by Fries et al. since specific cross-reactivity is observed only for M. intracellulare, M. avium, and M. paratuberculosis. Consequently, these probes are useful for clinical diagnosis of M. intracellulare and M. avium complex infection which currently comprise approximately 20% of pathogenic isolates in mycobacteriology laboratories (Good, R. E. et al.(1982) J. Infec. Dis. 146:829-33). Diagnosis is becoming important in management of HIV infection where an estimated 30-50% develop M. intracellulare or M. avium co infection (Morris, S. C. et al. (1991) J. Clin, Microbiol 29:2715 19). The probes of the invention are also useful for diagnosis of M. paratuberculosis infection implicated in Crohn's disease (Wayne, L. G. et al. (1992) Clin Microbiol.Rev. 5:1-25) and identified as the etiological agent of Johne's (veterinary) disease (Barclay et al. (1985) J. Bacteriology 164:896 903).

DETAILED DESCRIPTION

The present invention provides a probe having a seguence consisting essentially of Seq ID No:1-15, and the modified backbone (includes modified sugar and phosphates groups (e.g. thiophosphates)), modified nucleotide, labelled forms, and ribonucleic acid forms thereof.

A method of amplifying Mycobacterium avium, Mycobacterium intracellulare, and Mycobacterium paratuberculosis which comprises the use of one or more nucleic acid sequences selected from the sequences consisting essentially of Seq ID No:1 through 15, and ribonucleic acid forms thereof are also provided.

Also provided is a method of amplifying Mycobacterium avium, Mycobacterium intracellulare and Mycobacterium paratuberculosis and detecting the amplified product which comprises the use of one or more sequences selected from the sequences consisting essentially of Seq ID No:1-15, and the modified backbone, modified nucleotide, labelled forms, and ribonucleic acid forms thereof.

A kit comprising a nucleic acid sequence selected from the sequences consisting essentially of Seq ID No:1-15, and the modified backbone, modified nucleotide, labelled forms, and ribonucleic acid forms thereof is also provided.

Table 1 sets forth probes of the invention and where they hybridize to regions of the pMav29 clone identified in Molec. Cell. Probes 4:87 (1992) (left to right is 5'→3'):

TABLE 1

| Probe Sequence | Probe Sequence Position in pMav29* |
| --- | --- |
| (Seq ID No: 1) | |
| TGGCCAAACT GTGGGCGCAG GCCTGCGAGT GGGAACCGGT GACTCCAAAA ACCTTGCGGC TCTTACAAGT CGGTGGCGCC AAGCTGGAGC CCGAGGA | 72-168 |
| (Seq ID No: 2) | |
| TTGAATAGTC GGTTACTTGT TGACTCCTCG GGCTCCA | 156-168 |
| (Seq ID No: 3) | |
| TTGAAGTAAC CGACTATTGT TGACTGGCCA AACTGTG | 72-84 |
| (Seq ID No: 4) | |
| TTGAATAGTA GGTAAGTTGT TGACACTTGT AAGAGCC | 129-141 |
| (Seq ID No: 5) | |
| TTGAAGTAAC CGACTATTGT TGACTGCGAG | 95-107 |

TABLE 1-continued

| Probe Sequence | Probe Sequence Position in pMav29* |
|---|---|
| TGGGAAC (Seq ID No: 6) | |
| GGGAACCGGT GACTC (Seq ID No: 7) | 102–116 |
| CAAAAACCTT GCGGC (Seq ID No: 8) | 117–131 |
| AACCGGTGAC TCCA (Seq ID No: 9) | 105–118 |
| AAAACCTTGC GGC (Seq ID No: 10) | 119–131 |
| AACCGGTGAC TCCA (Seq ID No: 11) | 105–118 |
| GCGAGTGGGA ACCGGTGACT CCAAAAACCT TGCGGCTCTT ACAAGTC (Seq ID No: 12) | 96–142 |
| ACCGGTGACT CCAAAAACCT TGCGGCTCTT ACAAGTCGGT GGCGCCAAG (Seq ID No: 13) | 106–154 |
| GATCCCAGCC CCGAGGCGGC CTTCGCCAGT CGACCGCCAT GGCGTCACGG (Seq ID No: 14) | 1–50 |
| GGGAACCGGT GACTCCAAAA ACCTTGCGGC TCTTACAAGT CGGTGGCGCC (Seq ID No: 15) | 102–151 |
| GGCCAAACTG TGGGCGCAGG CCTGCGAGTG GGAACCGGTG ACTCCAAAAA CCTTGCGGCT CTTACAAGTC GGTGGCGCCA AGCTGGAGCC CGAGGACGCC CCGCCTG | 73–180 |

*Numbering according to pMav29 sequence having cytidine insert (See Example 1).

Probes of the invention are useful for amplifying nucleic acid sequences which hybridize to the probes. These nucleic acid sequences could then be cloned and used to express protein or an amino acid seguence based on the nucleic acid seguence or can be chemically synthesized. This amino acid seguence can then be used as an immunogen to make antibodies. Due to the degeneracy of the genetic code (many amino acids are selected by more than one codon) variations in the probe sequence will result in the same antibody specificity. Such antibodies can be polyclonal or monoclonal.

Probes of the invention can be deoxyribonucleic acid (DNA) or ribonucleic acid (RNA). DNA is composed of nucleotides based on purines (adenine and guanine) and pyrimidines (cytosine and thymine), with adenine base pairing (complementary) to thymine and guanine base pairing to cytosine. RNA is similar to DNA, except for the sugar differences (ribose instead of deoxyribose) and the base uracil, which is present instead of thymine. Also, modified nucleosides can be used in constructing probes of the invention. Modified nucleosides are typically used to obtain a probe capable of withstanding more stringent hybridization conditions, capable of easier detection, and the like. Preferably the probes are DNA.

The present invention can detect the presence of M. avium, M. intracellulare, M. paratuberculosis, all three, or any combination thereof, in a variety of samples. Samples can include clinical specimens such as fecal material, blood, sputum, saliva, urine, plague samples, tissue samples, fixed tissues, and tissue culture monolayers obtained by standard techniques such as lavage, scraping, or biopsy. The location or format of the Mycobacterium is not key to the invention, the ability to specifically detect, amplify, or isolate M. avium, M. intracellulare, M. paratuberculosis, or combination thereof, is key to the invention.

Samples obtained for use with probes of the invention can be utilized directly or amplified before using probes of the invention. A variety of amplification methods are available. For example, polymerase chain reaction (PCR), PCR Technology, H. A. Erlich, Ed. (Stockton Press, New York, N.Y., 1989), transcription based amplification system (TAS), Proc. Natl. Acad. Sci. USA. 86:1173 (1989), ligation amplification reaction (LAR), Genomics 4:560 (1989), ligase based amplification system (LAS), Gene 89:117 (1990), Strand displacement amplification (SDA) Proc. Natl. Acad. Sci, USA 89:392 (1992) and Nucleic Acids Res., 20:7 (1992), and Q B replicase, Infect. Dis. 162:13 (1990). The goal of any sample preparation is to eliminate false positives and improve sensitivity. Such a goal is obtained by taking into account the way samples are prepared, and the selection of a medium or substance in which the sample is prepared.

Probes of the invention can be prepared in a variety of ways and therefore are not limited to any particular preparation means. Suitable means for preparing the probes of the invention include using replication vectors and cloning the probe as a library, followed by appropriate screening procedures, and growing the vector in a suitable host. Purification and isolation will result in the probe being separated from the vector with select restriction enzymes. Preferably the probes are synthesized using commercially available methods and equipment. For example, the solid phase phosphoramidite method can be used to produce the probes of the invention. C. Caruthers, et al., Cold Spring Harbour Symp. Quant. biol., 47:411–418 (1982), and Adams, et al., J. Am. Chem. Soc., 105:601 (1983).

Typically, synthesis of nucleic acid probes utilize phosphoramidite derivatives that are appropriately protected for synthesis. See S. P. Adams et al., J. Am. Chem. Soc., 105:661 (1983), L. J. McBride and M. H. Caruthers, Tetrahedron Lett., 24:245 (1983), and N. D. Sinha et al., Nucleic Acids Res., 12:4539 (1984). Methods for incorporating phosphoramidites into a nucleic acid strand include the use of solid phase, solution phase, triesters, and H-phosphonate intermediates as generally illustrated by Froehler et al., *Nuc. Acids Res.*, 14:5399 (1986), Narang et al, *Methods Enz.*, 68:90 (1979) and Ogilvie, K. K. et al., *Proc., Natl. Acad. Sci. U.S.A.*, 85:5764 (1988).

Probes of the invention can be conventionally synthesized by the modified phosphotriester method using fully protected deoxyribonucleotide building blocks. Such synthetic methods can be carried out in substantial accordance with the procedure of Itakura et al., (1977), *Science,* 198:1056 and Crea et al., (1978), *Proc. Nat. Acad. Sci. U.S.A.*, 75:575, Hsiung et al., (1983), *Nucleic Acid Research,* 11:3227, and Narang et al., (1980), *Methods in Enzymology,* 68:90. In addition to manual procedures, the probes can be synthesized using automated synthesizers, such as the Systec 1450A or ABI 380A Synthesizers.

Probes of the invention can be utilized with naturally occurring sugar phosphate backbones as well as modified backbones including phosphorothioates, dithionates, alkyl phosphonates and α-nucleotides. Modified sugar phosphate backbones are generally illustrated by Miller and T'so, *Ann. Reports Med. Chem.*, 23:295 (1988) and Moran et al., *Nuc. Acids Res.*, 14:5019 (1987).

Use of probes in detection methods include Northern blots (RNA detection), Southern blots (DNA detection), western blots (protein detection), dot blots (DNA, RNA, or protein detection), and Slot blots (DNA, RNA or protein). Other detection methods include kits containing probes on a dipstick setup and the like.

To detect hybrid molecules formed from using the probes of the invention, typically a detectable marker is added to one of the probes. Probes can be labelled by several methods. Probes can be radiolabelled and detected by autoradiography. Such labels for autoradiography include $^3H$, $^{125}I$, $^{35}S$, $^{14}C$, and $^{32}P$. Typically the choice of radioactive isotopes depends on research preferences involving ease of synthesis, stability, and half lives of the isotopes. Other detectable markers include ligands, fluorophores, chemiluminescent agents, electrochemical labels, time resolved fluorophores, enzymes, and antibodies. Other detectable markers for use with probes of the invention include biotin, radionucleotides, enzyme inhibitors, co enzymes, luciferins, paramagnetic metals, spin labels, and monoclonal antibodies. The choice of label dictates the manner in which the label is bound to the probe.

Radioactive nucleotides can be incorporated into probes of the invention by several means. Such means include nick translation of double stranded probes, copying single-stranded M13 plasmids having specific inserts with the Klenow fragment of DNA polymerase I of *E. coli* or other such DNA polymerase in the presence of radioactive dNTP, transcribing cDNA from RNA templates using reverse transcriptase in the presence of radioactive dNTP, transcribing RNA from vectors containing strong promoters such as SP6 promoters or T7 promoters using SP6 or T7 RNA polymerase in the presence of radioactive rNTP, tailing the 3' ends of probes with radioactive nucleotides using terminal transferase, and by phosphorylation of the 5' ends of probes using gamma $^{32}P$ ATP and polynucleotide kinase.

Non radioactive probes of the invention can be labelled by indirect means. For example, a ligand molecule can be covalently bound to a probe of the invention. The ligand can then bind to an anti ligand molecule which is either inherently detectable or covalently bound to a signal system such as a detectable enzyme, a flourescent compound, or chemiluminescent compound.

Probes of the invention can also be conjugated directly to signal generating compounds by such means as conjugation with an enzyme. Suitable enzymes for labels include hydrolases, particularly phosphatases, esterases, glycosidases, and oxidoreductases such as peroxidases. Fluorescent compounds include fluorescein and derivatives thereof, rhodamine and derivatives thereof, dansyl, umbelliferone, and the like.

Various hybridization conditions can be employed when using probes of the invention. The particular hybridization technique is not essential to the invention. Hybridization techniques are generally described in "Nucleic Acid Hybridization, A Practical Approach", edited by Hanes, B. D. and Higgins, S. J., IRL Press, 1985, Gall and Pardue (1969), *Proc. Natl. Acad. Sci., USA,* 63:378–383, John Burnsteil and Jones (1969) *Nature* 223:582–587, and Southern, E., *J. Mol. Biol.* 98:503 (1975). With routine experimentation the conditions which permit satisfactory hybridization are easily obtained.

The correct hybridization complex can be detected in accordance with the label used with the probes. Therefore, the choice of label will guide the choice of detection methods. For example, when the label is a hapten or antigen, the hybridization complex can be detected using antibodies. Typically, the antibody will be attached to a flourescent or enzyme molecule which can be detected. Tijssen, P., "Practice in Theory of Enzyme Immunoassay, Laboratory Techniques in Biochemistry and Molecular Biology", Burdon, R. H., Van Knippenberg, P. H., Eds., Elsevier, 1985, PP.9–20. When the label is radioactive, the hybridization complex is exposed to X-ray film. Where the label is fluorescent, the sample is detected by irradiation with light of a particular wavelength. Enzyme labels are detected by incubation with appropriate substrate.

In addition to using probes of the invention for detecting sequences of mycobacteria, the probes of the invention can be used for isolating sequences of mycobacteria. In many diagnostic applications, merely detecting the presence of a seguence of mycobacteria in a sample is all that is desired. However, there are situations where it is desirable to isolate a seguence of mycobacteria. For example, a seguence can be isolated as a preliminary step to separate extraneous DNA and then the specific isolated DNA seguence is amplified using DNA amplification techniques.

Probes of the invention are also useful for amplification of mycobacteria sequences. For example, probes of the invention can be used as primers in a variety of amplification protocols such as polymerase chain reaction, transcription-based amplification system, ligation amplification reaction, ligase based amplification system and QB replicase (referenced above).

The probes of the invention can be conveniently provided in the form of a kit. The kits can also comprise probes in which detection can also be specific, for example, the probes can be designed for fluorescence, radioactive, and chemiluminescence detection.

The following examples illustrate the specific embodiments of the invention described in this document. As would be apparent to skilled artisans, various changes and modifications are possible and are contemplated within the scope of the invention described.

MATERIALS AND METHODS

Preparation of Capture Oligodeoxynucleotide Probe

The oligodeoxynucleotide capture probes were synthesized as described below. First, the capture oligomer was prepared using a DNA synthesizer (Model 380B, Applied Biosystems, Foster City, Calif.), and Biotin Ong TM reagent (Clonetech, Palo Alto, Calif.) such that there were three biotin molecules (BBB) at the 5' terminus of the oligodeoxynucleotide. Purification was accomplished by reverse phase High Pressure Liquid Chromatography (HPLC, Brownlee Lab Aquapore RP 300 Column-220 ×4.6 mm, C8 column 7 particle, 300 A pore size) with a UV monitor at 254 nm and a gradient of 14 to 44% Buffer B over one hour (Buffer B: 0.1M Triethylamine Acetate pH 7 with 50% Acetonitrile; Buffer A: 0.1M Triethylamine-Acetate, pH 7) and a flow rate of 1 ml/minute.

The oligodeoxynucleotide detector probes were synthesized using a DNA synthesizer (Model 380B, Applied Biosystems, Foster City, Calif.) and a 3'-aminomodifier column (Glenn Research, Sterling, Va.). This yielded an oligodeoxynucleotide with a 3' amine terminus required for subsequent conjugation with alkaline phosphatase. Calf intestine alkaline phosphatase (AP, enzyme immunoassay grade, Boehringer Mannheim, Indianapolis, Ind.) was dialyzed overnight at 4° C. against 50 mM potassium phosphate pH 7.5 and subsequently centrifuged to remove aggregates. The AP (4 mL, 10 mg/mL) was combined with a solution (40 uL) of succinimidyl 4-(p maleimidophenyl)butyrate (SMPB, obtained from Pierce, Rockford, Md., 50 mM) dissolved in N,N'-dimethylformamide (DMF, Aldrich, Milwaukee, Wis.) and allowed to react in the dark at room temperature for 30 minutes. The derivatized AP was purified using a NAP 25 column (Pharmacia, Piscataway, N.J.) previously equilibrated with 50 mM potassium phosphate pH 7.5 (degassed and purged with $N_2$). The absorbances of the NAP 25 column fractions were read at 260 and 280 nm using an extinction coefficient of 0.75 ml/umole cm$^{-1}$. Typically, about 170 nmoles of derivatized AP were obtained and stored on ice (less than 2 hours) until conjugation with the derivatized oligodeoxynucleotide.

The 3' amino-oligodeoxynucleotide (98.4 ul of 508.2 uM, 50 nmoles) was diluted in 13.4 ul of 1M potassium phosphate (pH 7.2) and mixed with 27 ul of a solution of n-succinimidyl-3-(2-pyridyldithio)propionate (50 mM, SPDP, Pierce, Rockford, Ill.) diluted in DMF. This mixture was incubated in the dark for 1 hour at room temperature. A solution of dithiothreitol (DTT, 1M) in 50 mM potassium phosphate (pH 7.5) was added to the oligodeoxynucleotide/DMF mixture to a final concentration of 0.1M DTT and allowed to incubate for 15 minutes at room temperature. Excess DTT and SPDP were separated from the derivatized oligodeoxynucleotide by elution over a NAP-25 column with 50 mM potassium phosphate (pH 7.5) Within 10 minutes of purification, the reduced oligodeoxynucleotide was mixed with the SMPB derivatized AP. Rapid mixture of the reduced oligomer and the SMPB derivatized AP is necessary to prevent reoxidation of the thiolated oligomer. The resulting solution was incubated 2 4 hours at room temperature, then overnight at 4° C. and quenched by addition of 1/100th the original volume of 50 mM beta-mercaptoethanol in 50 mM potassium phosphate (pH 7.5). The crude conjugate was concentrated using a Centriprep 30 TM centrifugal concentrator (Amicon, Danvers, Ma.) to approximately 2 ml. This material was further purified by HPLC using a DEAE-5PW column (7.5 mm×7.5 cm), a gradient of 0 to 66% Buffer B (Buffer B: 20 mM Tris, 1M NaCl pH 7.5, Buffer A: 20 mM Tris pH 7.5) and a flow rate of 1 ml/minute. Absorbance was monitored at 254 nm. Fractions with $A_{260}/A_{280}$ equal to 1 correspond to conjugate and were pooled. The protein concentration of the conjugated oligodeoxynucleotide was then determined (BCA Protein Assay Kit, Pierce, Rockford, Ill.).

The activities of the alkaline phosphatase (AP) detector oligodeoxynucleotide probes were determined as follows. The conjugate was diluted to 5 ug/ml in 50 mM Tris HCl, 100 mM NaCl, 1 mM $MgCl_2$, 1 mg/ml BSA, pH 7.5. The substrate, 4-nitrophenylphosphate (pNPP, 5mM), was dissolved in 1M diethanolamine, 1 mM $MgCl_2$, pH 9.8. AP activity was assayed as follows at 25° C. The conjugate (5 ul) was diluted into 2 ml of the substrate solution and the change in absorbance monitored at 405 nm using a Hewlet Packard 8452 spectrophotometer.

The reaction rates were calculated from the linear region of the kinetic plots using the extinction coefficient of p-nitrophenol at 405 nm (18500 $M^{-1}cm^{-1}$). The specific activity of the AP detector oligodeoxynucleotide probes were determined to be 850-1300 umole/minute/mg.

The purified AP detector oligodeoxynucleotide probe was diluted to 2 uM in 20 mM Tris, 1M NaCl, 0.05% sodium azide, 50 ug/ml sonicated salmon sperm DNA, pH 7.5, and stored thereafter at 4° C.

EXAMPLES

EXAMPLE 1

Development of *Mycobacterium avium/Mycobacterium intracellulare* Probe Sequences for Strand Displacement Amplification The target sequence for the invention was derived from the clone pMav29 as disclosed by Fries, J. M. W., et al. (1990) *Molec. Cell. Probes* 4:87–105. The specificity of this clone was tested against genomic DNA from a number of mycobacteria (pre-digested with the restriction endonuclease PstI) using Southern blot analysis (Southern, E. M. (1975) *J. Mol. Biol.* 98:503–517). Clone pMav29 was cross reactive to both *M. avium* and *M. intracellulare*, with lesser cross reactivity to *M. tuberculosis* and *M. bovis*. A similar clone, pMav22 was found to hybridize primarily to *M. avium* with lessor cross reactivity to *M. kansasii* and *M. intracellulare*. Fries et. al. continued work on pMav22 and developed a probe seguence specific for *M. avium*.

In order to identify a region of pMav29 specific for only *M. avium* and *M. intracellulare*, four 50 mer oligodeoxynucleotides were synthesized spanning the first 150 bases of pMav29 and a region from position 281–320 having relatively low GC/GCAT content. The oligomers were 5'-$^{32}$labelled using T4 polynucleotide kinase and used to probe Southern blots of PstI digests of various genomic DNA preparations (Table I). The blots were visualized by autoradiography using X-ray film. The film was placed next to the blot, then developed using standard procedures. Since the position of each preparation of genomic DNA on the blot is known, it is possible to determine the cross reactivity of the 5'-$^{32}$- labelled oligomers by the position of the dark spot (s) on the autoradiogram. That is, spots appear only where specific hybridization of 5'-$^{32}$P-labelled oligomers to membrane bound genomic DNA occurred. The results are presented in Table 2.

TABLE 1

Species Test for Cross reactivity in Southern Blot Analysis

*M. tuberculosis*
*M. scrofulaceum*
*M. kansasii*
*M. intracellulare*
*M. gordonae*
*M. fortuitum*
*M. chelonae*
*M. bovis*
*M. avium*
*Escherichia coli*
*Neisseria gonnorrhoeae*
Murine DNA isolated from McCoy cell tissue culture
DNA isolated from salmon sperm

TABLE 2

Specificity of pMav29 Oligomers in Southern Blot Analysis (Numbering is according to pMav29 sequence described by Fries et al.)

| Oligomer Position in pMav29 | Mycobacteria Species Cross Reactivity |
| --- | --- |
| 1-50 | *M. avium, M. intracellulare* |
| 51-100 | *M. avium, M. intracellulare, M. kansasii, M. gordonae, M. fortuitum, M. scrofulaceum* |
| 101-150 | *M. avium, M. intracellulare* |
| 72-167 | *M. avium, M. intracellulare* |
| 1-377 (pMav-29) | *M. avium, M. intracellulare, M. kansasii, M. bovis, M. tuberculosis* |

Initial Strand Displacement Amplification (SDA) experiments indicated that the region 72-167 of pMav29 would be amenable to amplification. Specificity of this region was determined by cloning/sequencing a Polymerase Chain Reaction (PCR) amplification product (position 72-167) obtained from *M. avium* genomic DNA. The seguence is in agreement with that published by Fries et. al. with the exception of a cytosine (C) insert between positions 93 and 94 of pMav29. The specificity of the clone having the C insert was rechecked as described above in Southern blot hybridization to PstI digested Mycobacterial DNA. This region (72-168, 97 bp) retains the original specificity of pMav29 (positions 72-167) for *M. avium* and *M. intracellulare* with negligible cross reactivity to other species (Table 2).

EXAMPLE 2

Displacement Amplification of *Mycobacterium avium-intracellulare* complex

As previously described, Southern Blot analysis of pMav29 indicated cross reactivity to *M. tuberculosis, M. kansasii* and *M. bovis* as well as *M. avium* and *M. intracellulare* (Table 2) Example 1.

Southern blot analysis of subsequences derived from the pMav29 clone indicated regions of specificity for *Mycobacterium avium* and *Mycobacterium intracellulare*. Based on this information, several other factors were considered: 1) G+C content should be close to 50%, 2) secondary structure should be minimal, 3) the target region should be large enough to accommodate the detector and capture probe.

Several regions of specificity based on Southern blot analysis were evaluated for G+C content. Bases 1-50 have specificity for *M. avium* and *M. intracellulare* but have a G+C content of 74%. Bases 105-153 (49 mer) and bases 95-141 (47 mer) showed G+C content of 55% and 53% respectively, which is close to the acceptable range.

Computer analysis of the secondary structure for these two potential target sequences was carried out. From this analysis it was noted that for the 49 mer target seguence, a hairpin due to a palindromic seguence could form between bases 144 and 151. The 47 mer target seguence showed no obvious secondary structure. However, one potential drawback for the 47 mer target was the relatively small number of nucleotides available for binding of detector and capture probes as discussed in following Example 3. With this in mind, SDA primer oligos were prepared for amplification of the 47 mer target.

Several primer sets and combinations were synthesized and tested for sensitivity. The best set of primers were chosen and tested under various conditions. Conditions that were evaluated included addition of glycerol or 1-methyl-2-pyrolidinone. Sensitivity of the assay was increased by the addition of glycerol. Assay sensitivity was increased even more by using 3% 1-methyl-2-pyrollidinone instead of 5-10% glycerol. Assembled reaction conditions contained the following:

Reaction Mix

50mM potassium phosphate pH 7,6
100 ug/ml bovine serum albumin
1 mM dithiothreitol
1 mM dCTP
1 mM dGTP
1 mM dATP alpha thio
1 mM TTP
6 mM magnesium chloride
3% (v/v) 1-methyl-2-pyrollidinone Enzymes 5 units exonuclease free klenow (United States Biochemicals, Cleveland, Ohio)
150 units HincII

| | Primer Mix |
| --- | --- |
| .05 uM | 5'TTGAATAGTCGGTTACTTGTTGACTCCTCGGGCTCCA3' (Seq ID No: 2) |
| .05 uM | 5'TTGAAGTAACCGACTATTGTTGACTGGCCAAACTGTG3' (Seq ID No: 3) |
| 0.5 uM | 5'TTGAATAGTAGGTAAGTTGTTGACACTTGTAAGAGCC3' (Seq ID No: 4) |
| 0.5 uM | 5'TTGAAGTAACCGACTATTGTTGACTGCGAGTGGGAAC3' (Seq ID No: 5) |

Two SDA primers (Seq ID No:2 and 4) bind to the anticoding strand and two SDA primers (Seq ID No:3 and 5) bind to the coding strand of the target genomic DNA seguence (Seq ID No:1).

All concentrations are final reagent concentrations in a sample volume of 50 ul. Target DNA was isolated from killed bacterial cells of *M. avium* and *M. intracellulare*. A series of stock target *M. avium* and *M. intracellulare* DNA solutions were assembled by dilution in the presence of 0.02 ug/uL of human DNA.

The SDA assay procedure consists of the following steps:

Add reaction mix to primer mix and target
Heat to 95° C. for 2 minutes
Cool to 37° C. for 5 minutes
Add enzymes and incubate at 37° C. for 2 hours
Stop reaction by heating to 95° C. for 3 minutes
Detect amplified product This procedure results in the detection of as few as 10 genomes of either *M. avium* or *M. intracellulare*.

EXAMPLE 3

The following procedure is provided to illustrate the method by which oligomers were identified for assay detection of *Mycobacterium avium* and *Mycobacterium intracellulare* DNA. First the seguence pMAV 29 was screened as described above in Southern blot hybridizations to determine appropriate specificity for *M. avium/intracellulare*. Second, conditions were developed which permit amplification of target DNA using SDA (also described above). Once amplification using SDA is established, a central region of amplified target exists for binding of assay oligomers. These oligomers must be designed to minimize competition with SDA primers. Also, the secondary structure of these oligomers must be minimized, including homo dimerization and heterodimerization. Finally, the melting temperature (Tm) must be adjusted to give high specificity for the target oligomer duplex, but not so as to reduce sensitivity of detection under the expected hybridization conditions. A number of methods are well known in the art for assessment of oligomer hybridization (secondary structure, dimerization, Tm). Especially useful are software packages such as Oligo TM (National Biosciences, Plymouth, Minn.) or PC Gene TM (Intelligenetics Inc., Geneva, Switzerland).

Design of oligomers for the detection of *M. avium/intracellulare* SDA products followed the above mentioned strategy. The internal region of the SDA product to be used for detection was 21 nucleotides long. In order to meet the needed specificity and Tm for the oligomers in the assay, the detection oligomers needed to overlap with the SDA oligomers. Competition was kept to a minimum while satisfying the requirements for hybridization. Detection oligomers were designed to be of 13–15 nucleotides in length. Homodimerization was kept between 2–8 bases, with the ideal conditions being 6–8 bases or less. Heterodimerization was held between 2–6 bases with the ideal being 3–5 bases or less. Any secondary structure (i.e., hairpin loops), was acceptable if the calculated Gibb's Free Energy was greater than −2.0 kcal/mole. In these examples, the Gibb's Free energy was generally between −2 and 3 kcal/mole for the most stable secondary structure as determined by computational methods (Oligo or PC Gene software). Melting temperature was dictated by oligomer concentration, %GC of the oligomer, and sodium chloride (NaCl) concentration and oligomer length. Oligomer concentration may range between 1–40 nM with the ideal being 5–20 nM. The NaCl concentration may range between 1–1000 mM with the ideal being 5–500mM NaCl. The %GC (G+C/G+C+A+T) may range from 40–80% with the preferred being 45–70%. The above factors may be adjusted to yield a calculated melting temperature of 20°–70° C., most preferably greater than 25° C.

EXAMPLE 4

Preparation of Coated Microtiter Plates

Biotinylated bovine serum albumin (biotin*BSA) (Pierce, Rockford, Ill.) was diluted to 1 ug/well in 0.3M Glycine pH 9.6 (BRL, Bethesda, Md., prepared using autoclaved water) and was pipetted into each well (200 ul/well) (Dynatech, Chantilly, Va.), and incubated at 4° C. overnight. The plates were washed twice (375 ul/wash) using FTA hemagglutination buffer (Becton Dickinson Microbiology Systems, Cockeysville, Md.) pH 7.2 prepared using autoclaved water. Streptavidin (5 ug/well) in hemaglutination buffer was added to the biotin*BSA coated microtiter wells (100 ul/well). Plates were covered and incubated for 1 hour at 37° C. Unbound streptavidin was discarded by inversion and blocking buffer (300 ul/well) (hemagglutination buffer pH 7.2, 0.05% w/v bovine serum albumin, Sigma Chemical Co., St. Louis, Mo.) was added. The plates were covered and incubated (30 min, 37° C.), and the blocking buffer discarded by inversion. Plates were washed twice with hemaglutination buffer (375 ul/well), then once using hemaglutination buffer with 2% w/v trehalose (375 ul/well) (Fluka, Ronkonkoma, N.Y.). Plates were dried for approximately 4 hours under vacuum below 0.5 Torr at 25° C., sealed in mylar pouches with desiccant, and stored overnight at room temperature prior to use. The plates were stored thereafter at 2°–8° C.

The assay uses 2 oligomers (probes), for detection of the SDA amplified target DNA. A biotinylated (BBB) capture probe for binding to the target DNA and the streptavidin on the microtiter plate. A second detector probe is conjugated with alkaline phosphatase (AP) and binds to the target DNA. The AP provides an opportunity for detection by means of colorimetry, fluorimetry, or chemiluminescence. This assay used the following probes for the detection of specific *Mycobacterium avium* and *Mycobacterium intracellulare* DNA amplified by SDA: Probe set 3.

5' BBB-A ACC GGT GAC TCC A 3' (Seq ID No: 10)

5' AAA-ACC TTG CGG C-AP 3' (Seq ID No: 9)

B: biotin
AP: Alkaline Phosphatase

Microtiter Plate Assay Procedure

SDA reactions (50 ul) containing 1000, 100, 10, 1, 0 genome copies/10 ul were prepared as follows: 35 ul of SDA reaction+140 ul of SDA dilution buffer ( 6.25 mM $KH_2PO_4$, 12.5 ug/ml BSA, 0.75 mM $MgCl_2$, 0.125 mM DTT, 0.375% glycerol, 0.375% NMP pH 7.6 +125 ug/ml sheared salmon sperm DNA (Sigma) were added to sterile siliconized tubes. Diluted SDA reactions were heated to 95° C. for 2 minutes to denature the DNA. Tubes were cooled for 5 minutes at room temperature and then 50 ul of the denatured SDA reaction was added to each well. Immediately thereafter, 50 ul/well of hybridization mix (1M sodium phosphate, 0.2% BSA, 40 nM capture probe, 10 nM detector probe) was added. The plate was covered and incubated for 45 minutes at 37° C. Three stringency washes (300 ul/well) (10 mM sodium phosphate pH 7, 0.1% w/v bovine serum albumin, 0.05% v/v Nonidet P-40) were performed at room temperature. Each wash was allowed to remain in the microtiter wells for 1 minute before removing. Lumiphos ™ 530 (100 ul/well, Lumigen Inc., Detroit, Mich.) substrate was added, and the plates were covered and incubated for 30 minutes at 37° C. Luminescence was read on a microtiter plate luminometer (Labsystems, Research Triangle Park, N.C.) at 37° C., using a 2 second/well integration time.

RESULTS

Using the above procedure, the assay detected 1–10 genomic copies of M. avium or M. intracellulare DNA (see Table 3 and Table 4).

TABLE 3

| Specific Signal - Relative Light Units (RLU) | |
|---|---|
| M. intracellulare genome copies | RLU's* |
| 1 | 58.82 |
| 10 | 174.09 |
| 100 | 9871.9 |
| 1000 | 7334.26 |

*Average of triplicate points; Background subtracted: zero = 55.4 RLU

EXAMPLE 5

Using the above example procedure, probes with a greater amount of competition with the SDA primers were compared to the previously mentioned capture and detector probes. The additional probes had the following sequences: Probe set 1

| 5' BBB-G GGA ACC GGT GAC TC 3' | (Seq ID No: 6) |
|---|---|
| 5' CAA AAA CCT TGC GGC-AP 3' | (Seq ID No: 7) |
| B: Biotin | |
| AP: Alkaline Phosphatase | |

RESULTS

The results show the significance of competition on the performance of the assay. While both sets of probes, 3 and 1, had minimal detectable levels of 1–10 genomic copies of M. avium, the effect of competition was seen by the decrease in sensitivity of the assay using probe set 1 with respect to that obtained using probe set 3 (Table 4). That is, probe set 1 exhibits reduced sensitivity due to increased competition with SDA primer oligodeoxynucleotides. Increased sensitivity provides for superior quantitation of amplified target and enhanced detection limits.

TABLE 4

| M. avium genome copies | *RLU's Probe Set 1 | *RLU's Probe Set 3 |
|---|---|---|
| 1 | 199.75 | 371.25 |
| 10 | 297.00 | 620.25 |
| 100 | 468.05 | 1337.60 |
| 1000 | 3358.50 | 9115.60 |

*Average of duplicate points; Background subtracted: zero for Set 1, 122 RLU; zero for set 3, 341.4 RLU.

SUMMARY

Methods are presented which teach how to design oligonucleotide reagents for detection of SDA amplified DNA from less than 10 copies of M. avium/intracellulare.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

EXAMPLE 6

Genomic DNA was isolated from organisms obtained from American Type Culture Collection, Brown University, the Trudeau Microbiological Collection, Laboratories Center Disease Control (Canada) and the Raleigh Veterans Administration Hospital. These specimens of DNA were then screened using aliquots of $10^6$ copies of purified genomic DNA and performing SDA and the microwell assay as described in substantial accordance with examples 2 and 4, above. The results were calibrated using assay results for synthesized target DNA and the apparent number of genomic copies was estimated for each specimen. In the cases of M. intracellulare, M. avium and M. paratuberculosis the number of copies was estimated to be above 1000. This is greater than the upper limit of the assay method. All other results were less than 17 estimated copies indicating a relative specificity (genomic copies added/genomic copies estimated) of greater than $10^6$ (Table 5). These results indicate high specificity for M. intracellulare, M. avium and M. paratuberculosis.

TABLE 5

| DNA Tested | # Genomic Copies Added | SDA/Assay Result, Genome equiv. |
|---|---|---|
| M. avium | $10^6$ | +,>1,000 |
| M. intracellulare | $10^6$ | +,>1,000 |
| M. paratuberculosis | $10^6$ | +,>1,000 |
| M. africanum | $10^6$ | −,<1 |
| M. bovis | $10^6$ | −,<1 |
| M. bovis BCG | $10^6$ | −,<1 |
| M. chelonae | $10^6$ | −,<1 |
| M. fortuitum | $10^6$ | −,<1 |
| M. gordonae | $10^6$ | −,<1 |
| M. kansasii | $10^6$ | −,<1 |
| M. microti | $10^6$ | −,<1 |
| M. tuberculosis | $10^6$ | −,<1 |
| M. scrofulaceum | $10^6$ | −,<1 |
| M. xenopi | $10^6$ | −,<1 |
| B. pertussis | $10^6$ | −,<1 |
| C. diptheriae | $10^6$ | −,<1 |
| R. rhodochrous | $10^6$ | −,<1 |
| E. coli | $10^6$ | −,10 |
| K. pneumoniae | $10^6$ | −,6 |
| N. lactamica | $10^6$ | −,10 |
| P. asteroides | $10^6$ | −,5 |
| P. aeruginosa | $10^6$ | −,6 |
| S. aureus | $10^6$ | −,5 |
| S. boydii | $10^6$ | −,6 |
| S. pneumoniae | $10^6$ | −,17 |
| S. pyogenes | $10^6$ | −,7 |

What is claimed is:

1. An oligonucleotide consisting of SEQ ID NO:1, SEQ ID NO:2, SEQ ID NO:3, SEQ ID NO:4, SEQ ID NO:5, SEQ ID NO:6, SEQ ID NO:7, SEQ ID NO: 9, SEQ ID NO: 10, SEQ ID NO:11, SEQ ID NO:12, SEQ ID NO:13, SEQ ID NO:14, SEQ ID NO:15, or ribonucleic acid forms thereof.

2. The oligonucleotide of claim 1 consisting of SEQ ID NO: 1.

3. The oligonucleotide of claim 1 consisting of SEQ ID NO: 2.

4. The oligonucleotide of claim 1 consisting of SEQ ID NO: 3.

5. The oligonucleotide of claim 1 consisting of SEQ ID NO: 4.

6. The oligonucleotide of claim 1 consisting of SEQ ID NO: 5.

7. The oligonucleotide of claim 1 consisting of SEQ ID NO: 6.

8. The oligonucleotide of claim 1 consisting of SEQ ID NO: 7.

9. The oligonucleotide of claim 1 consisting of SEQ ID NO: 9.

10. The oligonucleotide of claim 1 consisting of SEQ ID NO: 10.

11. The oligonucleotide of claim 1 consisting of SEQ ID NO: 11.

12. The oligonucleotide of claim 1 consisting of SEQ ID NO: 12.

13. The oligonucleotide of claim 1 consisting of SEQ ID NO: 13.

14. The oligonucleotide of claim 1 consisting of SEQ ID NO: 14.

15. The oligonucleotide of claim 1 consisting of SEQ ID NO: 15.

16. The oligonucleotide of claims 1 through 16 which is the ribonucleic acid form thereof.

17. A method of amplifying *Mycobacterium avium, Mycobacterium intracellulare,* or *Mycobacterium paratuberculosis* nucleic acid sequences comprising hybridizing an oligonucleotide primer consisting of SEQ ID NO:1, SEQ ID NO:2, SEQ ID NO:3, SEQ ID NO:4, SEQ ID NO:5, SEQ ID NO:6, SEQ ID NO:7, SEQ ID NO: 9, SEQ ID NO: 10, SEQ ID NO:11, SEQ ID NO:12, SEQ ID NO:13, SEQ ID NO:14, SEQ ID NO:15, or ribonucleic acid forms thereof to Mycobacterium nucleic acids in a sample and amplifying the Mycobacterium nucleic acid sequences by extension of the primer.

18. A method of detecting *Mycobacterium avium, Mycobacterium intracellulare,* or *Mycobacterium paratuberculosis* nucleic acid sequences which comprises hybridizing an oligonucleotide probe consisting of ID NO:1, SEQ ID NO:2, SEQ ID NO:3, SEQ ID NO:4, SEQ ID NO:5, SEQ ID NO:6, SEQ ID NO:7, SEQ ID NO: 9, SEQ ID NO: 10, SEQ ID NO:11, SEQ ID NO:12, SEQ ID NO:13, SEQ ID NO:14, SEQ ID NO:15, or ribonucleic acid forms thereof to Mycobacterium nucleic acid sequences in a sample and detecting hybridization by means of a detectable marker included in or conjugated to the probe.

19. A method of amplifying *Mycobacterium avium, Mycobacterium intracellulare,* or *Mycobacterium paratuberculosis* nucleic acid sequences and detecting the amplified products which comprises hybridizing an oligonucleotide primer consisting of ID NO:1, SEQ ID NO:2, SEQ ID NO:3, SEQ ID NO:4, SEQ ID NO:5, SEQ ID NO:6, SEQ ID NO:7, SEQ ID NO: 9, SEQ ID NO: 10, SEQ ID NO:11, SEQ ID NO:12, SEQ ID NO:13, SEQ ID NO:14, SEQ ID NO:15, or ribonucleic acid forms thereof.

20. A kit comprising an oligonucleotide primer or probe consisting of ID NO:1, SEQ ID NO:2, SEQ ID NO:3, SEQ ID NO:4, SEQ ID NO:5, SEQ ID NO:6, SEQ ID NO:7, SEQ ID NO: 9, SEQ ID NO: 10, SEQ ID NO:11, SEQ ID NO:12, SEQ ID NO:13, SEQ ID NO:14, or SEQ ID NO:15, or ribonucleic acid forms thereof and reagents for use with the primer or probe for amplification or detection of Mycobacterium nucleic acid sequences in a sample.

21. The oligonucleotide of claim 1 conjugated to a detectable marker.

22. The oligonucleotide of claim 21 wherein the detectable marker is selected from the group consisting of radioactive isotopes, ligands, fluorophores, chemiluminescent agents, electrochemical labels, enzymes and antibodies.

23. The oligonucleotide of claim 1 incorporating a detectable marker.

24. The oligonucleotide of claim 23 wherein the detectable marker is a radioactive isotope or a ligand.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TGGCCAAACT GTGGGCGCAG GCCTGCGAGT GGGAACCGGT GACTCCAAAA ACCTTGCGGC    60
TCTTACAAGT CGGTGGCGCC AAGCTGGAGC CCGAGGA                             97
```

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TTGAATAGTC GGTTACTTGT TGACTCCTCG GGCTCCA                             37
```

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
TTGAAGTAAC CGACTATTGT TGACTGGCCA AACTGTG                             37
```

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TTGAATAGTA GGTAAGTTGT TGACACTTGT AAGAGCC                             37
```

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
TTGAAGTAAC CGACTATTGT TGACTGCGAG TGGGAAC                             37
```

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGGAACCGGT GACTC         15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CAAAAACCTT GCGGC         15

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AACCGGTGAC TCCA         14

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AAAACCTTGC GGC         13

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AACCGGTGAC TCCA         14

( 2 ) INFORMATION FOR SEQ ID NO:11:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:11:

GCGAGTGGGA ACCGGTGACT CCAAAAACCT TGCGGCTCTT ACAAGTC     47

(2) INFORMATION FOR SEQ ID NO:12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:12:

AACCGGTGAC TCCAAAAACC TTGCGGCTCT TACAAGTCGG TGGCGCCAAG     50

(2) INFORMATION FOR SEQ ID NO:13:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:13:

GATCCCAGCC CCGAGGCGGC CTTCGCCAGT CGACCGCCAT GGCGTCACGG     50

(2) INFORMATION FOR SEQ ID NO:14:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:14:

GGGAACCGGT GACTCCAAAA ACCTTGCGGC TCTTACAAGT CGGTGGCGCC     50

(2) INFORMATION FOR SEQ ID NO:15:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:15:

GGCCAAACTG TGGGCGCAGG CCTGCGAGTG GGAACCGGTG ACTCCAAAAA CCTTGCGGCT     60

CTTACAAGTC GGTGGCGCCA AGCTGGAGCC CGAGGACGCC CCGCCTG     107